US00RE36521E

United States Patent [19]

Hiemisch

[11] E Patent Number: Re. 36,521

[45] Reissued Date of Patent: Jan. 18, 2000

[54] CONNECTING PART BETWEEN LEG PROSTHESIS COMPONENTS

[75] Inventor: Christian Hiemisch, Duderstadt, Germany

[73] Assignee: Otto Bock Orthopaedische Industrie Besitz - und Verwaltungs KG, Duderstadt, Germany

[21] Appl. No.: 08/730,210

[22] Filed: Oct. 15, 1996

Related U.S. Patent Documents

Reissue of:

[64] Patent No.: 5,405,406
Issued: Apr. 11, 1995
Appl. No.: 08/041,242
Filed: Apr. 1, 1993

[30] Foreign Application Priority Data

Apr. 1, 1992 [DE] Germany ..... 92 04 448 U

[51] Int. Cl.[7] ..... A61F 2/62

[52] U.S. Cl. ..... 623/38; 403/90

[58] Field of Search ..... 623/39–42, 38, 623/43, 44–46; 403/84, 90, 362

[56] References Cited

U.S. PATENT DOCUMENTS

| | | | |
|---|---|---|---|
| 3,659,294 | 5/1972 | Glabiezewski . | |
| 4,969,911 | 11/1990 | Greene | 623/38 |
| 5,013,325 | 5/1991 | Rennerfelt | 623/38 |
| 5,047,063 | 9/1991 | Chen | 623/38 |
| 5,156,632 | 10/1992 | Wellershaus | 623/55 |

FOREIGN PATENT DOCUMENTS

| | | | |
|---|---|---|---|
| 0497686 | 8/1992 | European Pat. Off. | 623/38 |
| 1584288 | 12/1969 | France . | |
| 2630641 | 11/1989 | France . | |
| 1922619 | 10/1976 | Germany . | |
| 2617075 | 11/1976 | Germany | 623/43 |
| 499982 | 12/1970 | Switzerland . | |
| 1217404 | 3/1986 | U.S.S.R. | 623/38 |
| 1553115 | 3/1990 | U.S.S.R. | 623/38 |
| 2087727 | 6/1982 | United Kingdom | 623/33 |

OTHER PUBLICATIONS

Fillauer Inc. Parts: Fillauer Inc., product brochure, Durr–Fillauer Orthopedic, Inc. product brochure, and sale invoice dated Jan. 31, 1992.

*Primary Examiner*—David H. Willse
*Attorney, Agent, or Firm*—Foley & Lardner

[57] ABSTRACT

A connecting part of a ball joint between leg prosthesis components with a flange intended to fasten to the one component, the flange having an adjusting element position on it, consisting of a cup and a four-sided pyramid positioned centrally upon its point. To improve the adjustability of the connecting part, the flange is a rectangular flange with four holes, upon which the adjusting element is eccentrically positioned.

9 Claims, 3 Drawing Sheets

CONNECTING PART BETWEEN LEG PROSTHESIS COMPONENTS

Matter enclosed in heavy brackets [ ] appears in the original patent but forms no part of this reissue specification; matter printed in italics indicates the additions made by reissue.

BACKGROUND OF THE INVENTION

The invention relates to the connecting part of a ball joint between leg prosthesis components with a flange, intended to attach to one of the components, on which there is an adjusting element, which consists of a cup and four-sided pyramid set on its point on the center of the cup.

A corresponding embodiment can be derived from German Patent No. 19 22 619. In this case, the adjusting element composed of the cup and the pyramid is placed exactly in the middle of the attachment flange. By adjusting either of the two positional screws placed opposite each other, the ball joint can be adjusted in only two defined levels. This makes it possible, for example, to position a leg prosthesis advantageously on the load axis.

This previously known adaptor is generally used to connect the prosthetic substitute system to the prosthetic shaft for lower leg stumps and short to medium-long upper leg stumps. In the case of poor stump positioning, for example in the flexing and/or splaying direction, which can be found in particular in the constantly growing group of geriatric patients with amputated legs, in some circumstances it may be necessary in designing the prosthesis to use most of the adjustment area which is available in each direction but which is limited by its construction, so that the remaining adjustable area is no longer sufficient for adjustment according to bio-mechanical criteria.

SUMMARY OF THE INVENTION

One purpose of the invention is to improve the adjustability of the initially described connecting part.

This purpose is accomplished in accordance with the invention by making the flange a rectangular flange with four holes, to which the adjusting element is eccentrically attached.

In accordance with the invention, as embodied and broadly described herein, a connecting part of a ball joint for connecting first and second leg prosthesis components comprises a flange adapted to be fastened to the first leg prosthesis component; and an adjusting element positioned on the flange, the adjusting element including a cup and a four-sided pyramid positioned centrally upon the cup on its point; wherein the flange is a rectangular flange having four holes; and wherein the adjusting element is eccentrically set upon the flange.

By rotating the rectangular four-holed flange in 90° segments around its central axis defined by the circular centering collar, it is now possible to make a center skew notch in the adjusting element in various directions for compensatory pre-positioning, without having to make use of the direction-specific adjusting field to any noticeable degree.

Various possible embodiments of the principle in accordance with the invention, as well as the implementation will be explained in greater detail using the explanatory examples.

Additional objects and advantages of the invention will be set forth in the description which follows and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given bellow, serve to explain the principles of the invention.

The drawings show two embodiments of the invention which serve as examples and a state-of-the-art embodiment. The following are shown.

DETAILED DESCRIPTION OF THE PREFERRED EMBODIMENTS

Figure 5:
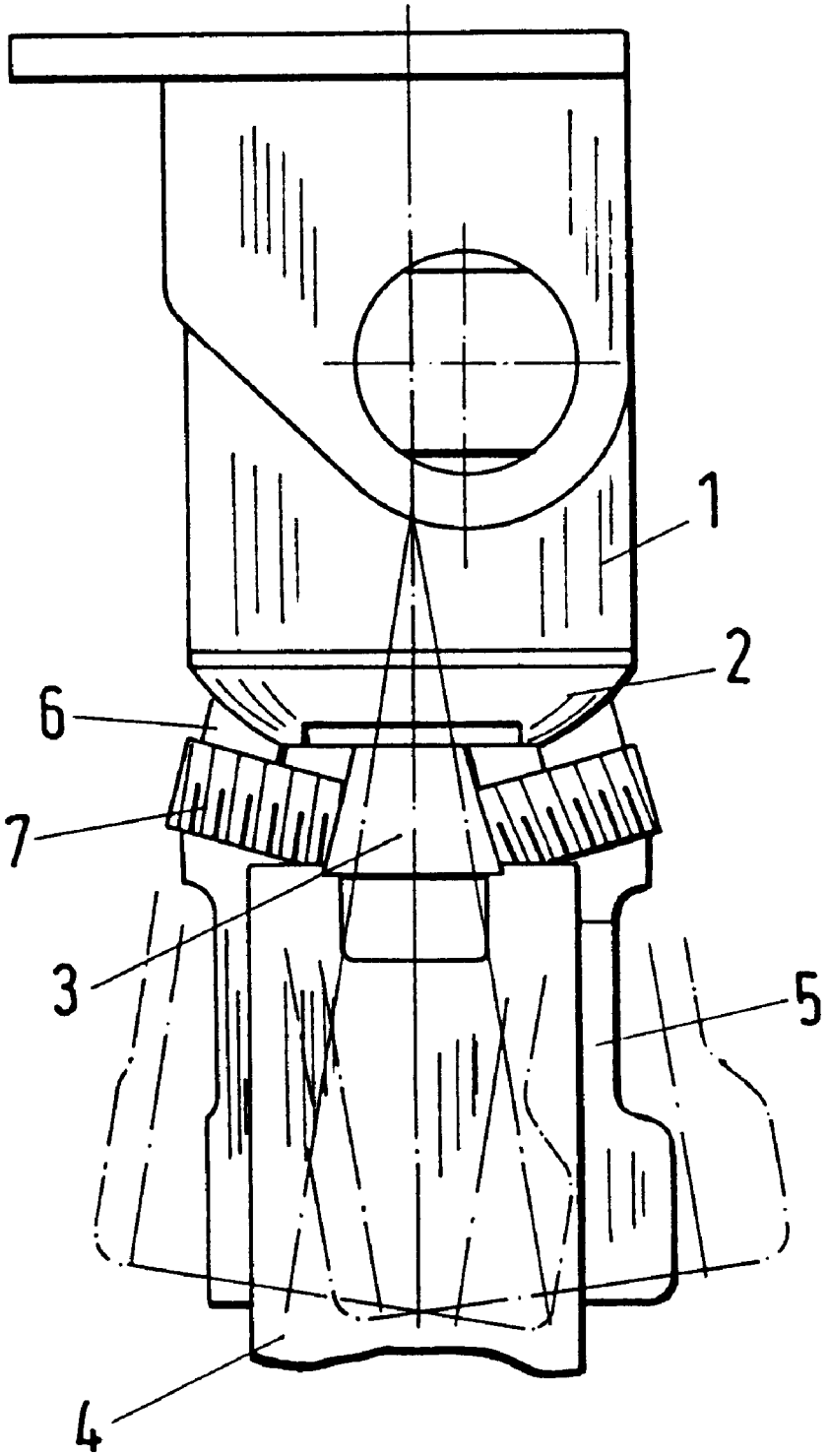
Fig. 5 PRIOR ART
FIG. 5—a ball joint connection between two leg prosthesis components, known from the prior art, shown schematically in side view and partly in longitudinal view.

FIG. 5 shows an illustration from the previously published German Patent No. 19 22 619. Attached to a leg prosthesis component 1 is a flange (not illustrated in greater detail) on which an adjusting element is placed, composed of cup 2 and a four-sided pyramid 3 positioned centrally on the cup on its point. A bushing 5 is attached to the upper end of a second leg prosthesis component 4 in FIG. 5 and its upper free end is constructed as ball socket 6, which rests on cup 2 and has four boreholes in its surrounding shell, set at 90 degrees to each other and threaded on the inside, each with set screw 7 threaded into it, the inner end of which lies against the attached wall of the four-sided pyramid 3.

By loosening one set screw 7 and correspondingly tightening the opposing set screw, the adjustable ball joint can be swung in one defined plane and, upon corresponding adjustment of the two other set screws 7, in a second swinging plane perpendicular to the first plane. Adjustment of the two set screws 7 illustrated in FIG. 5 thus brings about a swinging of the second leg prosthesis component 4, illustrated in the diagram, within the plane of projection in accordance with the dot and dash illustrations. In this way, for example, the adjustment of a leg prosthesis can be set to the load axis. By loosening two adjacent set screws 7, the two leg prosthesis components 1,4 can be separated, during which process the two unloosened set screws 7 ensure that when the two components are reconnected, the previously set angular position can be found again. The advantage of this construction is thus that the angle of the two leg prosthesis components 1,4 to one another is adjusted by swinging in only two defined planes each, and that each desired angle position can be fixed and can be found again even after the two components have been separated.

Figure 1:
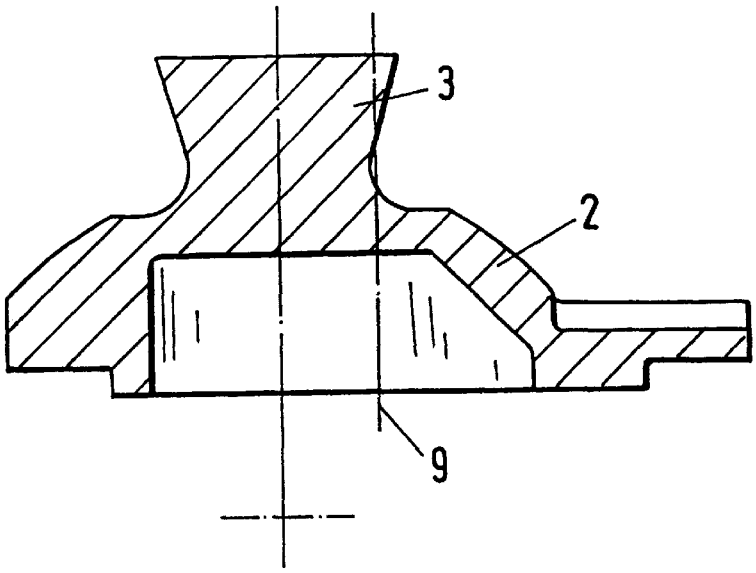
FIG. 1—a connecting part in cross-section.
Figure 2:
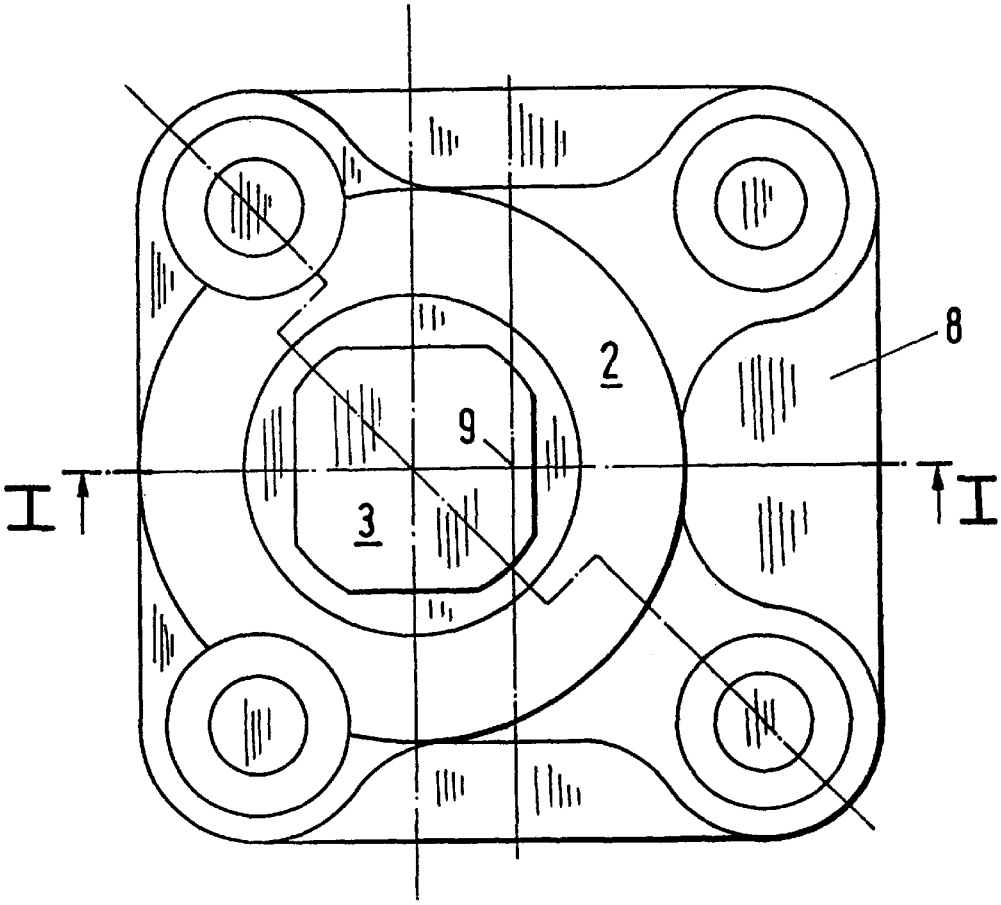
FIG. 2—the connecting part as in FIG. 1, from above.

FIGS. 1 and 2 show an embodiment in accordance with the invention for one connecting part of the ball joint described above. The design provides for a rectangular four-holed flange 8 on which the adjusting element composed of the cup 2 and the pyramid 3 is eccentrically positioned. This also applies to the modified embodiment in accordance with the invention, as shown in FIGS. 3 and 4.

Figure 3:
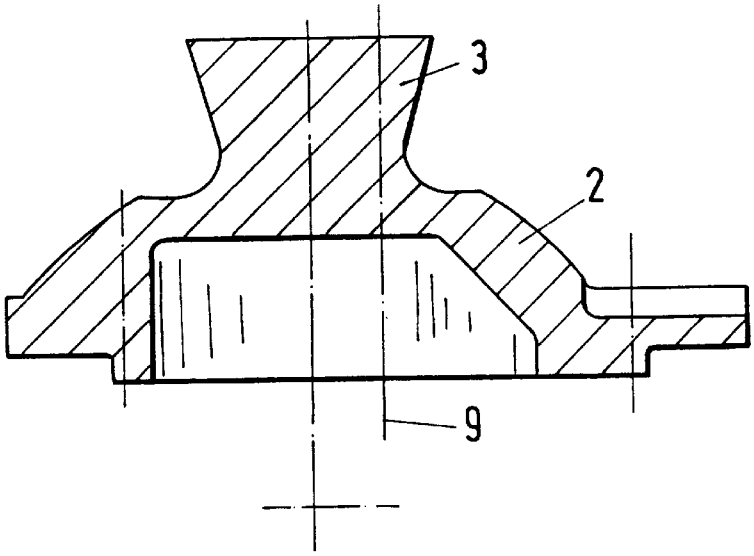
FIG. 3—a modified embodiment illustrated as in FIG. 1.
Figure 4:
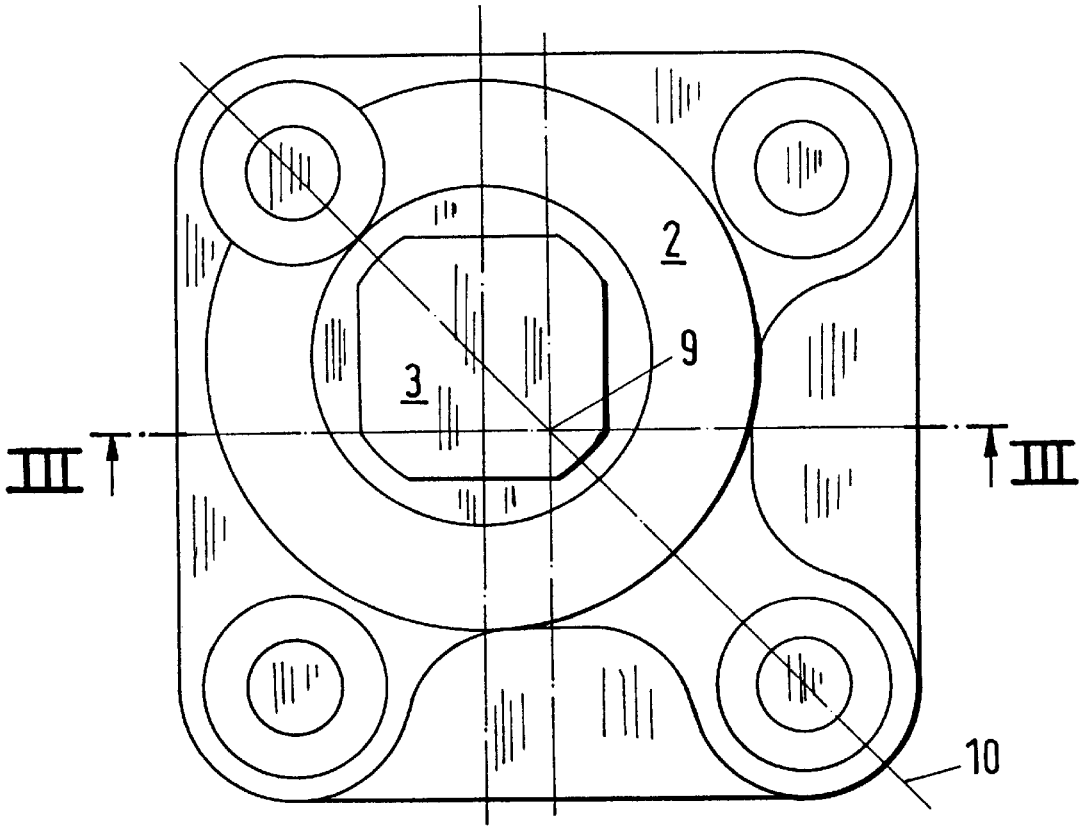
FIG. 4—a top view of the embodiment illustrated in FIG. 3.

In the embodiment as in FIGS. 1 and 2, the central skew notch of the adjusting element 2,3 which is opposite the central axis 9 defined by the circular centering collar of the flange 8, is made on a central line parallel to two flange edges, whereas in the embodiment in accordance with FIGS. 3 and 4 the central skew notch is made on one of the flange diagonals 10.

By rotating the rectangular four-holed flange 8, which is identical in the two embodiments in accordance with the invention, in 90° segments around its central axis 9, it is possible to set a central skew notch of the adjusting element 2,3 for compensatory pre-positioning; specifically, this is forward, outward, backward or inward in the embodiments in accordance with FIGS. 1 and 2 and forward/outward, outward/backward, backward/inward and inward/forward in the embodiment in accordance with FIGS. 3 and 4. In this regard, it is especially the flexibility of the backward and inward positions (embodiment in accordance with FIGS. 1 and 2) or the backward/inward positions (embodiment in accordance with FIGS. 3 and 4) that is of particular importance for the usual treatment.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

[1. A connecting part of a ball joint for connecting first and second leg prosthesis components comprising:

a flange adapted to be fastened to the first leg prosthesis component; and an adjusting element positioned on the flange, the adjusting element including a cup and a four-sided pyramid having an apex, the pyramid being positioned centrally upon the cup on the apex defining a central axis;

wherein the flange is a rectangular flange having a central axis and four holes; and wherein the adjusting element is eccentrically set upon the flange, that is, wherein the central axes are substantially parallel and offset.]

2. The connecting part according to claim [1] *5*,wherein the adjusting element includes a central skew notch.

3. The connecting part according to claim 2, wherein the central skew notch provides compensatory pre-positioning in forward, outward, backward, and inward directions.

4. The connecting part according to claim 2, wherein the central skew notch provides compensatory pre-positioning in forward/outward, outward/backward, backward/inward, and inward/forward directions.

5. [The] *A* connecting part [according to claim 1,] *of a ball joint for connecting first and second leg prosthesis components comprising:*

*a flange adapted to be fastened to the first leg prosthesis component; and*

*an adjusting element positioned on the flange, the adjusting element including a cup and a four-sided pyramid having an apex, the pyramid being positioned centrally upon the cup on the apex defining a central axis;*

*wherein the flange is a rectangular flange having a central axis and four holes;*

*wherein the adjusting element is eccentrically set upon the flange, that is, wherein the central axes are substantially parallel and offset; and* wherein the adjusting element and the flange are one piece.

6. The connecting part according to claim [1] *5*,wherein each of the four holes has a central longitudinal axis parallel to the central axis of the flange.

7. [The] *A* connecting part [according to claim 6,] *of a ball joint for connecting first and second leg prosthesis components comprising:*

*a flange adapted to be fastened to the first leg prosthesis component; and*

*an adjusting element positioned on the flange, the adjusting element including a cup and a four-sided pyramid having an apex, the pyramid being positioned centrally upon the cup on the apex defining a central axis;* wherein the flange *has a central axis and four holes, and* is rectangular in a plane orthogonal to the central axis of the flange[.]*;*

*wherein the adjusting element is eccentrically set upon the flange, that is, wherein the central axes are substantially parallel and offset;*

*wherein each of the four holes has a central longitudinal axis parallel to the central axis of the flange; and*

*wherein the flange and the adjusting element are monolithic.*

*8. A connecting part of a ball joint for connecting first and second leg prosthesis components comprising:*

*a flange having a central axis and four holes, the holes extending through the flange; and*

*an adjusting element set upon the flange, the adjusting element including a cup and a four-sided pyramid having an apex, the apex being positioned centrally upon the cup to define an adjusting element central axis that is substantially parallel to and offset from the central axis of the flange;*

*wherein the flange and the adjusting element are contiguous;*

*wherein the four holes are positioned in the flange at corners of a rectangular pattern that lies orthogonal to the central axis of the flange.*

*9. The connecting part according to claim 8, wherein the flange and at least a portion of the adjusting element comprise the same material.*

*10. The connecting part according to claim 8, wherein each of the four holes has a central longitudinal axis parallel to the central axis of the flange.*

* * * * *